United States Patent [19]
Harari

[11] Patent Number: 5,579,784
[45] Date of Patent: Dec. 3, 1996

[54] MALE CONDOM

[76] Inventor: Max M. A. Harari, Carrera 68 No. 21-85, Bogotá, Colombia

[21] Appl. No.: 409,333

[22] Filed: Mar. 23, 1995

[51] Int. Cl.⁶ .................................................. A61F 6/04
[52] U.S. Cl. .................................................. 128/844; 128/918
[58] Field of Search ................................. 128/842, 844, 128/918; 604/347–353

[56] References Cited

U.S. PATENT DOCUMENTS

| | | | |
|---|---|---|---|
| 2,604,092 | 7/1952 | Brown | 128/844 |
| 3,037,508 | 6/1962 | Friedman | 128/844 |
| 3,282,414 | 11/1966 | Penksa | 128/844 |
| 3,648,700 | 3/1972 | Warner | 128/844 |
| 4,821,742 | 4/1989 | Phelps | 128/844 |
| 5,163,449 | 11/1992 | van der Valk | 128/844 |
| 5,199,444 | 4/1993 | Wheeler | 128/844 |
| 5,479,940 | 1/1996 | Babled | 128/844 |

*Primary Examiner*—Michael A. Brown
*Attorney, Agent, or Firm*—Vaden, Eickenroht & Thompson

[57] ABSTRACT

There are disclosed two embodiments of a male condom, one of which covers only the head of the penis and the other of which is adapted to cover the fully length thereof. In each case, an elastic band is secured about the open end of the condom to fit tightly about the penis, and is mounted on a fitting ring which permits the user to hold it expanded as the condom is placed over the penis and then permits the band to be released and tightly engage the head of the penis as its end is pushed against the closed end of the condom.

4 Claims, 3 Drawing Sheets

FIG.1
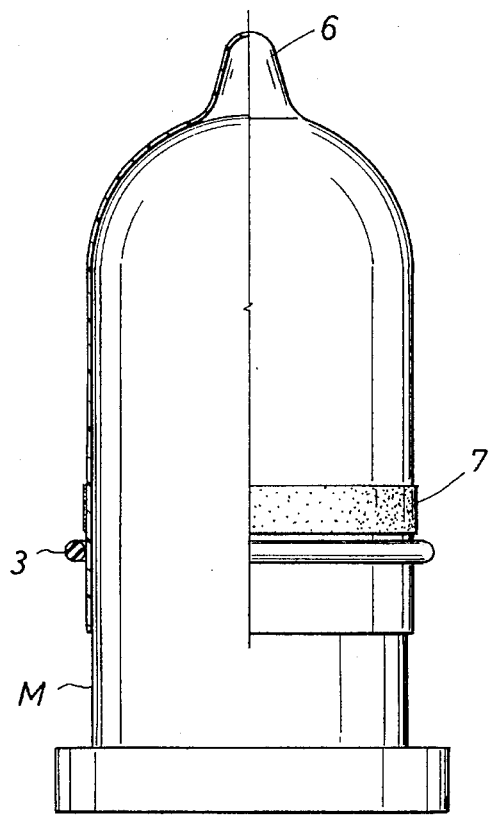
FIG.2
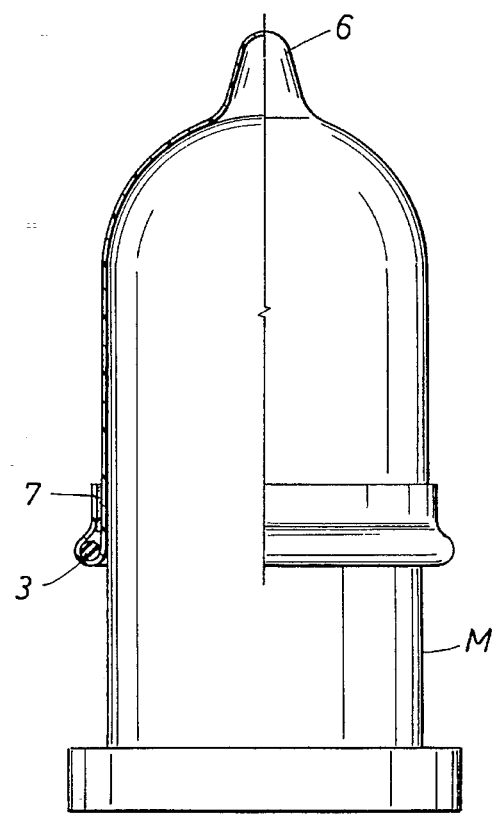
FIG.3
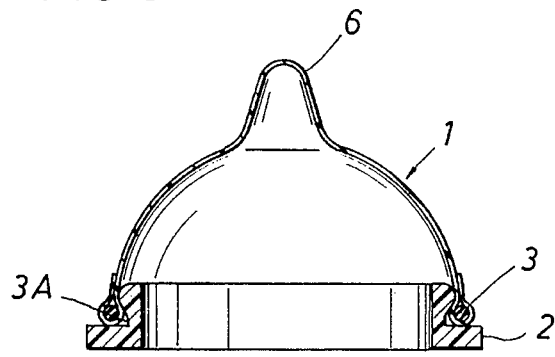
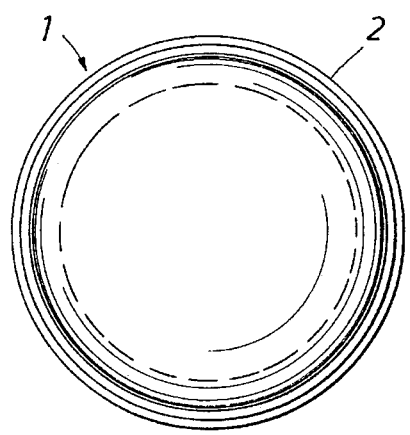
FIG.4

MALE CONDOM

FIELD OF THE INVENTION

The following invention comprises a male condom, which, in one embodiment, is characterized by its limited coverage to the head of the penis and otherwise by its easy method of securing to the penis and improved sensitivity.

DESCRIPTION OF THE PRIOR ART

Since medieval times, the concept of the condom as a means to prevent the man's semen from being deposited in the woman's cervix, and hence preventing insemination, is known. Aside from being a birth control method, another main purpose of the condom is to prevent sexually transmitted diseases, such as syphilis, gonorrhea, chlamydia, herpes, and of great interest currently, the acquired immune deficiency syndrome (AIDS). Given its public health importance, the condom has had to evolve in different ways and according to the user's necessities.

Currently, the most known condom is certainly one made of latex which the user unrolls to cover the penis from its head to the public base. Although this condom works reasonably well to block the passage of sperm if properly placed and secured, it has various inherent problems, including the latex of which it is made. Because of the variations in the thickness of the latex condom's wall, which is a result of the dipping manufacturing method, it is easy to leave a minute hole in the latex, typically on the condom's head, that later could be the point of a total rupture during intercourse, or simply could permit the free passage of spermatozoa or bacterial or viral agents. In an attempt to prevent these holes, some latex condoms have been fabricated with a greater wall thickness, thereby reducing the possibility of leaving a hole, but at the same time causing a serious loss in heat transfer and sensitivity, two very important characteristics in a condom.

Another problem with latex is that it needs to be stored in optimum conditions, that is, away from heat, cold, or pressure (i.e. not in a wallet in a rear pocket); otherwise, the latex crystallizes, thereby losing its elasticity and increasing the possibility of a rupture. A proposed solution for this problem at a technical level has been to use materials like polyurethane which is stronger than latex and does not degrade as easily; however, one encounters heat transfer and sensitivity problems again. Likewise, condoms made of other elastomers, polyolefins or combinations of these have been proposed. For example, see U.S. Pat. Nos. 4,855,169 (McGlthlin, et al.), 4,808,174 (Sorkin), 4,817,593 (Taller et al.) and 4,576,156 (Dyck et al.).

Another serious problem of the common condom is its design, which permits easy slippage during intercourse, or later, when the penis is flaccid. The slippage statistics for the condom vary, but for example, an article in Semana (Bogota, Colombia, Feb. 16, 1994) quotes Stuart Tovey, a British researcher, who, through an interview with 280 men, observed that 50% had had the condom slip, and 25% had had a rupture. One reason for the high slippage rate is simply the incorrect placement of the condom, for example, the user does not unroll it completely. Given the fact that the standard size of condoms is 180 millimeter (7 inches), it is sometimes physically impossible for the user to unroll the condom completely. Another reason for the loosening is that the condom's design and material (an elastomer) forces it to roll itself back after being unrolled, especially when not unrolled completely. This tendency to roll itself back is further aggravated by the fact that every time that the penis is introduced inside the vagina, the vaginal walls firmly grasp the condom and pull the open end toward the head, thus further increasing the chances the condom will roll itself back again and finally slip off. Likewise, another reason for the loosening of the condom is the penis' flaccidity that normally occurs after ejaculation, which causes the condom to no longer be in contact with the penis (i.e. the condom is no longer stretched over the penis).

One solution to this slippage problem is found in McGlthlin, et al., U.S. Pat. No. 4,855,169, who proposes significantly increasing the condom's wall thickness in the area proximal to the pubic area, this way making it harder for the condom to roll itself back up. Another solution was given by Sorkin, U.S. Pat. Nos. 4,808,174 and 4,955,392, which essentially covers the entire penis including the pubic zone, using an adhesive which maintains the condom stuck to the skin in the pubic zone. Another solution was proposed by Wheller, U.S. Pat. No. 5,199,444, which suggests using a retention ring in the proximal part to the pubic zone (see FIG. 1) or, alternatively an internal adhesive seal located also in the same area.

Another serious problem in the common condom's design is its placement. From a practical point of view, there is no doubt that, when fitting a condom, the user typically has no time to cautiously read the instructions, much less verify if the condom has been placed on correctly. It is known that the condom's correct placement is crucial for its optimum functionality, but nevertheless, a system that offers a method for easy, fast and correct placement has not been found.

BRIEF DESCRIPTION OF THE INVENTION

An object of the present invention is to present a condom made of a secure material, but at the same time thin, sensitive and with good heat transfer.

Another object of the present invention is to present a condom to be fitted easily, even without having the penis erect.

Another object of the present invention is to present a condom that only covers totally and securely, the penis' head.

The following invention is a condom chiefly characterized, in one embodiment, by its limited coverage of the penis' head, although another embodiment covers the entirety of the penis' body, and its fabrication of a polyolefinic material, typically a low density polyethylene. The condom adjacent its open end, includes a rubber band (or other elastic), which fits tightly around the penis and behind the head in the one embodiment, in this manner holding the condom on the penis. In order to more securely retain the band on the condom, its open end may be turned back and secured to the outer side of the strip to capture the band. Thus the open end may be sealed to itself by heat and pressure or a thin strip of medical adhesive may be adhered about the circumference of the condom in close proximity to the rubber band and the condom adhered to the outer side of the strip.

The system to fit the condom on the penis consists of a separate fitting ring on which the condom is releasably mounted by expanding the band to snap into a groove about the ring. The fitting ring is large enough so that the penis can fit through it, and, when the penis is pushed sufficiently hard against the condom, this causes the band of the condom to snap loose from the ring and snap inwardly correctly and automatically around and behind the penis' head. The complete fitting process once the condom package is opened does not take longer than five seconds if the penis is erect. The invention also works if the penis is not erect as it only requires that the rubber band be attached around and behind the penis' head.

Another embodiment of the present invention also includes a polyolefinic condom which also uses the same fitting ring, but which, instead of covering only the head, covers the entirety of the penis in order to provide greater protection from sexually transmitted diseases for the user.

DESCRIPTION OF THE DRAWINGS

FIG. 1 is a sectional view of a condom as it is stretched down over a male mold, and with the elastic band and the adhesive strip in place;

FIG. 2 is a view similar to FIG. 1, but with the open end of the condom turned back on itself and adhered to the adhesive strip to capture the band;

FIG. 3 is an enlarged sectional view of the prepared condom of FIG. 2 removed from the mold an having its open end stretched over the ring and into a groove thereabout;

FIG. 4 is a top view of the closed end of the condom, looking down in FIG. 3;

DETAILED DESCRIPTION OF THE INVENTION WITH REFERENCE TO THE DRAWINGS

Figure 5:
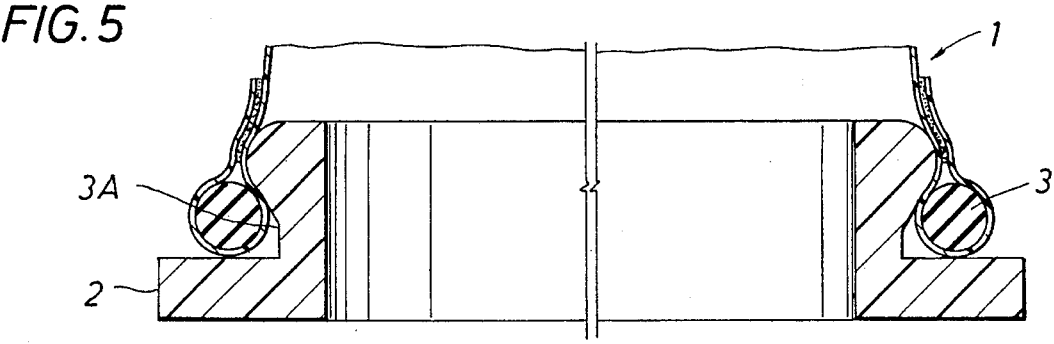
FIG. 5 is an enlarged sectional view of the band in the open end of the condom, held within the groove about the fitting ring.
Figure 6:
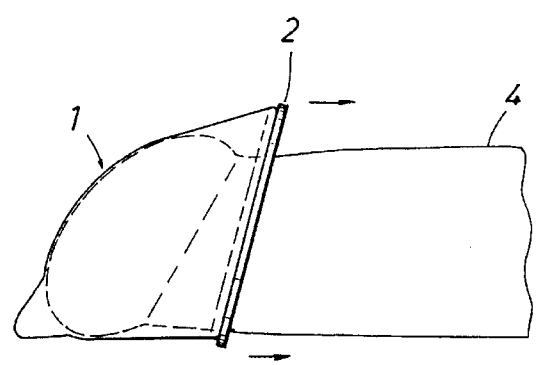
FIG. 6 is a side view of the first mentioned embodiment of the condom as it is pulled over the head of the penis.

Making reference to the drawings, and the embodiment of FIGS. 3 to 7, the condom 1 shown in FIGS. 3 to 6 is of a length to provide coverage limited to the penis' head and with open end releasably attached to a fitting ring 2. Disposed around the open end of the condom 1, during placement, is a band of rubber or other elastic material which maintains the condom 1 attached to the fitting ring 2, as well as eventually to the penis' head 5. The rubber band 3 is attached to the condom by turning its open end on itself to wrap the lip of the condom around the rubber band and then securing it to the outside of the condom by using a combination of pressure/heat and an adhesive, which in the preferred embodiment is an adhesive transfer tape (927 made by 3M), in order to capture the band. The tightness of the rubber band should be sufficient to maintain an adequate seal around the head of the penis, but not tight enough to restrict blood circulation or cause undue discomfort to the user.

Preferably, a thin strip of medical adhesive 7 is adhered around the circumference of the condom, in close proximity to the rubber band 3, so that the condom may be adhered to its outer side when turned back. In the preferred embodiment, the medical adhesive tape of choice is a double coated medical tape transfer adhesive (width 0.25 in.) made by 3M, so that, after one side is adhered to the condom, the lip of the condom may be secured to its outer side to capture the band.

Preferably, the condom's design should also contain a small receptacle 6 for the deposit of semen after ejaculation.

The condom's material can be any polyolefin, although a low density polyethylene works optimally since it gives good sensitivity, heat conduction, and resistance against rupture. Low density polyethylene also demonstrates excellent adhesion that permits the walls of the condom to always be in contact with the penis' head, in this manner offering protection even when the penis is flaccid. After experimenting, the wall thickness with optimum characteristics for the condom was of 0.0003 millimeters (without stretching), which in turn is an order of magnitude (ten times) thinner than latex condoms which have thicknesses of approximately 0.0040 millimeters.

The condom can be manufactured by using a high quality polyethylene film (Mobilwrap MAX and F have worked satisfactorily) and stretching it over a mold male M, as shown in FIGS. 1 and 2, until the desired shape and wall thickness are reached, applying concepts well-known by those versed in the prior art. Once stretched, the rubber band can be incorporated around the condom's lip using a combination pressure/heat seal and the adhesive strip, as shown in FIG. 2. The condom is then placed on another machine which stretches the elastic band to permit its open end to be placed in a groove 3A about the fitting ring, at which point it can be packed. As best shown in FIG. 5, the grooved essential "V" shaped and has a conical surface to enable it to snap out of the groove as it is placed over the penis.

The fitting ring 2 can be fabricated of any material such as nylon, and preferably polypropylene, which is rigid enough to maintain the condom open. Preferably, the material should be the least expensive possible since the ring is disposable. Likewise, the ring's internal diameter should be large enough so as to move freely over the erect penis as it is installed (see FIG. 9B).

In another embodiment of the same invention, the condom 1A is of a length to cover the entire penis, having a rubber band snapping down over the base of the penis (instead of over the head), when released from fitting ring 2A to place the condom. As in the case of condom 1, a strip of medical/surgical adhesive in close proximity to the rubber band is also advisable as an additional security measure.

Figure 7:
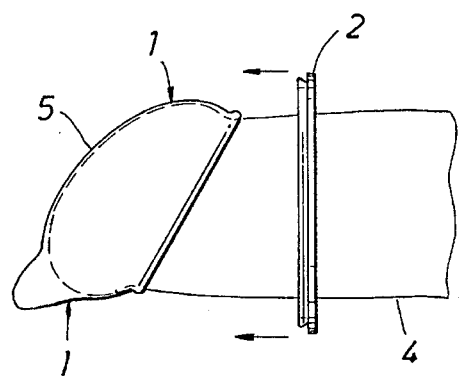
FIG. 7 is a view similar to FIG. 6, but following release of the band from the ring for fitting over the end of the penis, and as the ring is being removed therefrom.
Figure 8:
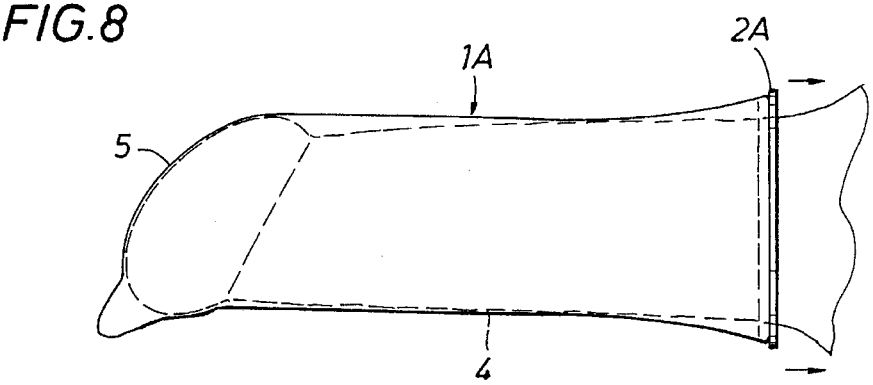
FIG. 8 is a view of another embodiment of the condom as it is pulled over the length of a penis.
Figure 9A:
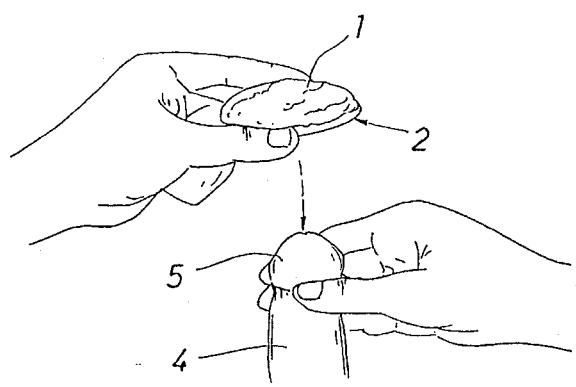
FIGS. 9A, 9B, 9C and 9D illustrate successive steps in the placement of the condom over only the head of the penis.
Figure 9B:
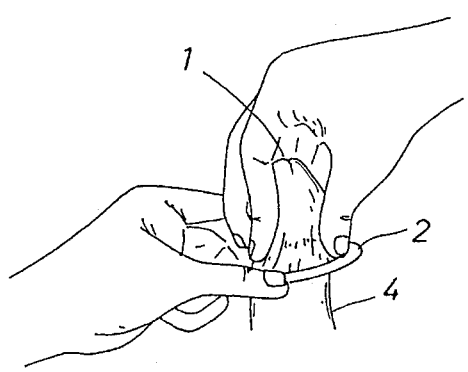
Figure 9C:
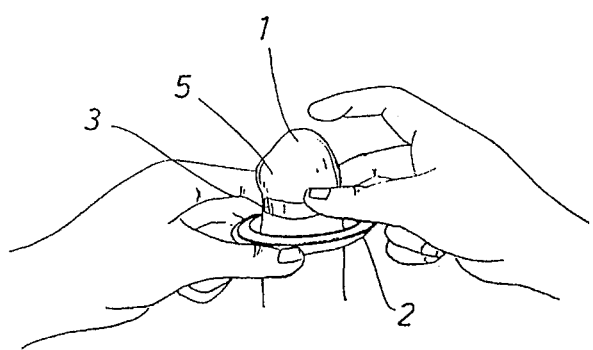
Figure 9D:
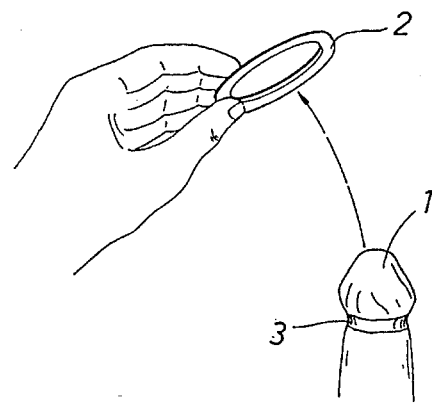

The process of placing either the condom 1 or 1A is simple, fast and the possibilities of committing an error are minimal. Making reference to FIG. 2A, one observes condom 1 and the fitting ring 2 above the penis 4 immediately before placement. In FIG. 9B as well as FIG. 6, the penis 4 has pierced the ring 2 and is exerting pressure over the condom 1, this way stretching it and forcing it to snap off the ring 2, as shown in FIGS. 9C and 7, into a position in which the ring 2 is below the penis' head 5, thus permitting the rubber band 3 to automatically tightly engage and securely fasten around and behind the head 5 when the condom 1 snaps off from the ring 2. Fastening of the condom to the penis' head is achieved by a combination of the rubber band 3, by the high adhesion of the condom's polyolefin to the penis' head, and, if used, a medical adhesive strip around the inner circumference of the condom. It is important to note that, in contrast to current condoms, this invention does not have any tendency to roll back since the polyolefin does not have a "memory" like latex does.

Placing the version of the condom 1A which covers the entirety of the penis' body is also accomplished the same way as described above, except that the fitting ring 2A must obviously be pulled all the way back to the base of the penis.

From the foregoing it will be seen that this invention is one well adapted to attain all of the ends and objects hereinabove set forth, together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. For use in practicing birth control, an assembly comprising;

a condom having an elastic band secured thereto adjacent its open end for fitting tightly about the penis, and means adapted to be grasped by the user for holding the open end of the condom expanded as it is placed on the penis and from which the band is then released to permit the band to fit about the penis as the holding means is removed therefrom, said holding means comprising a ring which maintains the band in an expanded position as the condom is placed over the penis and then releases the band to contract tightly about the penis as the tip of the condom is forced inwardly against the end of the penis, and the open end of the condom being doubled over the band and adhesively bonded to itself to capture the band.

2. As in claim 1, wherein the open end of the condom is adhesively bonded to itself by a strip which has adhesive on both its inner and outer sides so that one side may be adhered to the one surface of the condom and the other surface of the condom may be adhered to its outer side.

3. As in claim 1, wherein the open end of the condom is secured to itself by heat and pressure.

4. As in claim 1, wherein the ring has a groove thereabout to receive the expanded band during placement of the condom and from which the band is freed so that the ring may then be removed over the condom and end of the penis.

* * * * *